(12) United States Patent
Eisinger

(10) Patent No.: US 11,523,828 B2
(45) Date of Patent: Dec. 13, 2022

(54) SEALED RELOAD ASSEMBLY FOR STAPLING DEVICE

(71) Applicant: Covidien LP, Mansfield, MA (US)

(72) Inventor: Joseph Eisinger, North Haven, CT (US)

(73) Assignee: Covidien LP, Mansfield, MA (US)

( * ) Notice: Subject to any disclaimer, the term of this patent is extended or adjusted under 35 U.S.C. 154(b) by 156 days.

(21) Appl. No.: 17/120,968

(22) Filed: Dec. 14, 2020

(65) Prior Publication Data

US 2021/0228211 A1 Jul. 29, 2021

Related U.S. Application Data

(60) Provisional application No. 62/966,695, filed on Jan. 28, 2020.

(51) Int. Cl.
*A61B 17/115* (2006.01)
*A61B 17/00* (2006.01)
*A61B 17/072* (2006.01)

(52) U.S. Cl.
CPC .... *A61B 17/1155* (2013.01); *A61B 2017/0053* (2013.01); *A61B 2017/00486* (2013.01); *A61B 2017/07257* (2013.01); *A61B 2017/07271* (2013.01); *A61B 2017/07285* (2013.01)

(58) Field of Classification Search
CPC ............ A61B 17/068; A61B 17/07221; A61B 17/1155; A61B 17/115
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Gloria R Weeks
(74) *Attorney, Agent, or Firm* — Carter, DeLuca & Farrell LLP

(57) ABSTRACT

A stapling device includes a handle assembly, an adaptor assembly extending from the handle assembly, and a reload assembly supported on a distal end portion of the adaptor assembly. The reload assembly includes a shell housing, a staple cartridge, a first seal, a staple actuator, and a knife carrier. The first seal is disposed within a cavity of the shell housing and defines a staple actuator opening and a knife carrier opening. The staple actuator includes a proximal leg extending proximally therefrom and through the staple actuator opening of the first seal to provide a fluid seal therebetween. The knife carrier includes a proximal body portion extending proximally therefrom and through the knife carrier opening of the first seal to provide a fluid seal therebetween.

17 Claims, 6 Drawing Sheets

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A * | 12/1984 | Shichman ............ A61B 17/115 227/179.1 |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant ................... A61B 17/115 227/19 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |

(56) References Cited

U.S. PATENT DOCUMENTS

| | | |
|---|---|---|
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |

(56) References Cited

U.S. PATENT DOCUMENTS

| | | |
|---|---|---|
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |

(56) References Cited

U.S. PATENT DOCUMENTS

| | | | |
|---|---|---|---|
| 10,537,331 B2 | 1/2020 | Scirica et al. | |
| 10,542,993 B2 | 1/2020 | Guerrera et al. | |
| 10,548,598 B2 | 2/2020 | Prescott et al. | |
| 10,561,424 B2 | 2/2020 | Penna et al. | |
| 10,568,631 B2 | 2/2020 | Rebuffat et al. | |
| 10,575,847 B2 | 3/2020 | Hessler et al. | |
| 10,595,871 B2 | 3/2020 | Racenet et al. | |
| 10,595,872 B2 | 3/2020 | Milliman | |
| 10,603,042 B2 | 3/2020 | Sgroi | |
| 10,624,646 B2 | 4/2020 | Bae et al. | |
| 10,639,041 B2 | 5/2020 | Williams | |
| 10,653,414 B2 | 5/2020 | Williams | |
| 11,253,255 B2* | 2/2022 | Eisinger | A61B 17/0686 |
| 2003/0111507 A1 | 6/2003 | Nunez | |
| 2004/0217146 A1* | 11/2004 | Beck | A61B 17/115 227/176.1 |
| 2005/0051597 A1 | 3/2005 | Toledano | |
| 2005/0107813 A1 | 5/2005 | Gilete Garcia | |
| 2005/0187576 A1* | 8/2005 | Whitman | A61B 17/1155 227/176.1 |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2014/0046352 A1 | 2/2014 | Reboa et al. | |
| 2014/0158747 A1 | 6/2014 | Measamer et al. | |
| 2014/0284370 A1 | 9/2014 | Sahin | |
| 2015/0083772 A1 | 3/2015 | Miller et al. | |
| 2015/0173763 A1 | 6/2015 | Liu | |
| 2015/0209045 A1 | 7/2015 | Hodgkinson et al. | |
| 2016/0143641 A1 | 5/2016 | Sapienza et al. | |
| 2016/0157856 A1 | 6/2016 | Williams et al. | |
| 2016/0302792 A1 | 10/2016 | Motai | |
| 2021/0022731 A1* | 1/2021 | Eisinger | A61B 17/1155 |
| 2021/0228211 A1* | 7/2021 | Eisinger | A61B 17/1155 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3498185 A1 | 6/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| RU | 2025093 C1 | 12/1994 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2005037084 A2 | 4/2005 |
| WO | 2008107918 A1 | 9/2008 |

OTHER PUBLICATIONS

European Examination Report from Appl. No. 14181908.6 dated May 3, 2016.

Extended European Search Report issued in corresponding application EP 21153622.2 dated Mar. 30, 2021 (7 pages).

* cited by examiner

SEALED RELOAD ASSEMBLY FOR STAPLING DEVICE

CROSS-REFERENCE TO RELATED APPLICATIONS

This application claims the benefit of and priority to U.S. Provisional Patent Application Ser. No. 62/966,695 filed Jan. 28, 2020, the entire disclosure of which is incorporated by reference herein.

FIELD

This disclosure is generally related to surgical stapling devices and, more particularly, to surgical stapling devices and reload assemblies for surgical stapling devices that include a sealed configuration.

BACKGROUND

Powered surgical stapling devices include a handle assembly, an adaptor assembly including a distal portion supported on the handle assembly, and a tool assembly (e.g., a staple cartridge) supported on the distal portion of the adaptor assembly. Some include a shell or reload assembly that has a staple cartridge, a staple pusher, and an annular knife. The staple cartridge supports one or more annular rows of staples, and the staple pusher is movable within the staple cartridge to eject the staples from the staple cartridge. The annular knife is positioned radially inward of the annular rows of staples and is movable from a retracted position to an advanced position to cut or core tissue. The annular knife can be movable simultaneously with the staple pusher or independently of the staple pusher to cut tissue during a surgical procedure, e.g., an anastomosis procedure.

In some applications, some components of the stapling device are disposable while others are reusable after proper sterilization. Proper sterilization of reusable components is more difficult and time consuming if contaminants can flow into the adaptor assembly.

SUMMARY

This disclosure is directed to a surgical stapling device and to reload assemblies for surgical stapling devices that include a sealed configuration to prevent ingress of fluids therein.

In accordance with aspects of the disclosure, a stapling device includes a handle assembly, an adaptor assembly extending from the handle assembly, and a reload assembly supported on a distal end portion of the adaptor assembly. The reload assembly includes a shell housing, a staple cartridge, a first seal, a staple actuator, and a knife carrier. The shell housing defines a cavity and has a proximal portion and a distal portion. The staple cartridge is supported on the distal portion of the shell housing. The first seal is disposed within the cavity and defines a staple actuator opening and a knife carrier opening. The staple actuator is disposed within the cavity of the shell housing and movable relative to the shell housing to eject a plurality of staples from the staple cartridge. The staple actuator includes a proximal leg extending proximally therefrom and through the staple actuator opening of the first seal to provide a fluid seal therebetween. The knife carrier is disposed within the cavity of the shell housing and movable relative to the shell housing. The knife carrier includes a proximal body portion extending proximally therefrom and through the knife carrier opening of the first seal to provide a fluid seal therebetween.

In an aspect, the staple actuator defines a longitudinal bore and the knife carrier is movable through the longitudinal bore.

In an aspect, the reload assembly further includes a knife secured to the knife carrier and being movable with the knife carrier as the knife carrier is moved.

In an aspect, the knife includes an annular cutting edge.

In an aspect, the stapling device includes a coupling mechanism adapted to secure the reload assembly to the distal end portion of the adaptor assembly.

In an aspect, the reload assembly further includes a bushing disposed within a cylindrical cavity defined by the shell housing configured to receive a trocar of the adaptor assembly therethrough. In an aspect, the reload assembly further includes a second seal operably coupled to an inner annular surface of the bushing such that a fluid seal is formed between the bushing and a trocar when a trocar is positioned therethrough. In an aspect, the first seal defines a central opening and the bushing is positioned through the central opening.

In an aspect, the staple actuator opening of the first seal is curved along a surface of the first seal to match a curved shape of the proximal leg of the staple actuator.

In accordance with aspects of the disclosure, a reload assembly is provided including a shell housing, a staple cartridge, a first seal, a staple actuator, and a knife carrier. The shell housing defines a cavity and has a proximal portion and a distal portion. The staple cartridge is supported on the distal portion of the shell housing. The first seal is disposed within the cavity and defines a staple actuator opening and a knife carrier opening. The staple actuator is disposed within the cavity of the shell housing and movable relative to the shell housing to eject a plurality of staples from the staple cartridge. The staple actuator includes a proximal leg extending proximally therefrom and through the staple actuator opening of the first seal to provide a fluid seal therebetween. The knife carrier is disposed within the cavity of the shell housing and movable relative to the shell housing. The knife carrier includes a proximal body portion extending proximally therefrom and through the knife carrier opening of the first seal to provide a fluid seal therebetween.

In an aspect, the staple actuator defines a longitudinal bore and the knife carrier is movable through the longitudinal bore.

In an aspect, the reload assembly includes a knife secured to the knife carrier and being movable with the knife carrier as the knife carrier is moved. The knife may include an annular cutting edge.

In an aspect, the reload assembly further includes a bushing disposed within a cylindrical cavity defined by the shell housing configured to receive a trocar of the adaptor assembly therethrough. In an aspect, the reload assembly further includes a second seal operably coupled to an inner annular surface of the bushing such that a fluid seal is formed between the bushing and a trocar when a trocar is positioned therethrough. In an aspect, the first seal defines a central opening and the bushing is positioned through the central opening.

In an aspect, the staple actuator opening of the first seal is curved along a surface of the first seal to match a curved shape of the proximal leg of the staple actuator.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects of the disclosure are described herein below with reference to the drawings, wherein.

DETAILED DESCRIPTION

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel including doctors, nurses, and support personnel.

The aspects of the disclosed reload assembly and stapling device utilizing the disclosed reload assembly provide one or more seals that prevent fluid ingress into components of the reload assembly and stapling device. The powered EEA adaptor is a reusable device that is designed to be cleaned and used again in several procedures. Because tissue and fluids can enter the device through a distal opening in the adaptor, it is necessary to clean inside the adaptor prior to reuse. To assist with this cleaning, a trocar of the adaptor is removed prior to cleaning to allow greater access to the interior of the adaptor. This can present challenges in the reliability of the trocar being inserted and removed properly by clinicians.

The disclosure describes use in the powered EEA (or other applicable medical devices) to incorporate a seal in the reload to prevent fluid ingress into the device and components of the device including the adaptor. The seal or seals can combine to create a barrier to entry of bodily soils to the interior of the device.

In accordance with this disclosure, a trocar can be fixed to a reload assembly and not removed therefrom for cleaning. This will make it less dependent on clinicians to assemble and disassemble the device, and reduce cost and potential for error. By placing one or more seals in the reload assembly, the adaptor can be less complex and still allow the device to be cleaned should any small amount of soil get past the seals.

Figure 1:
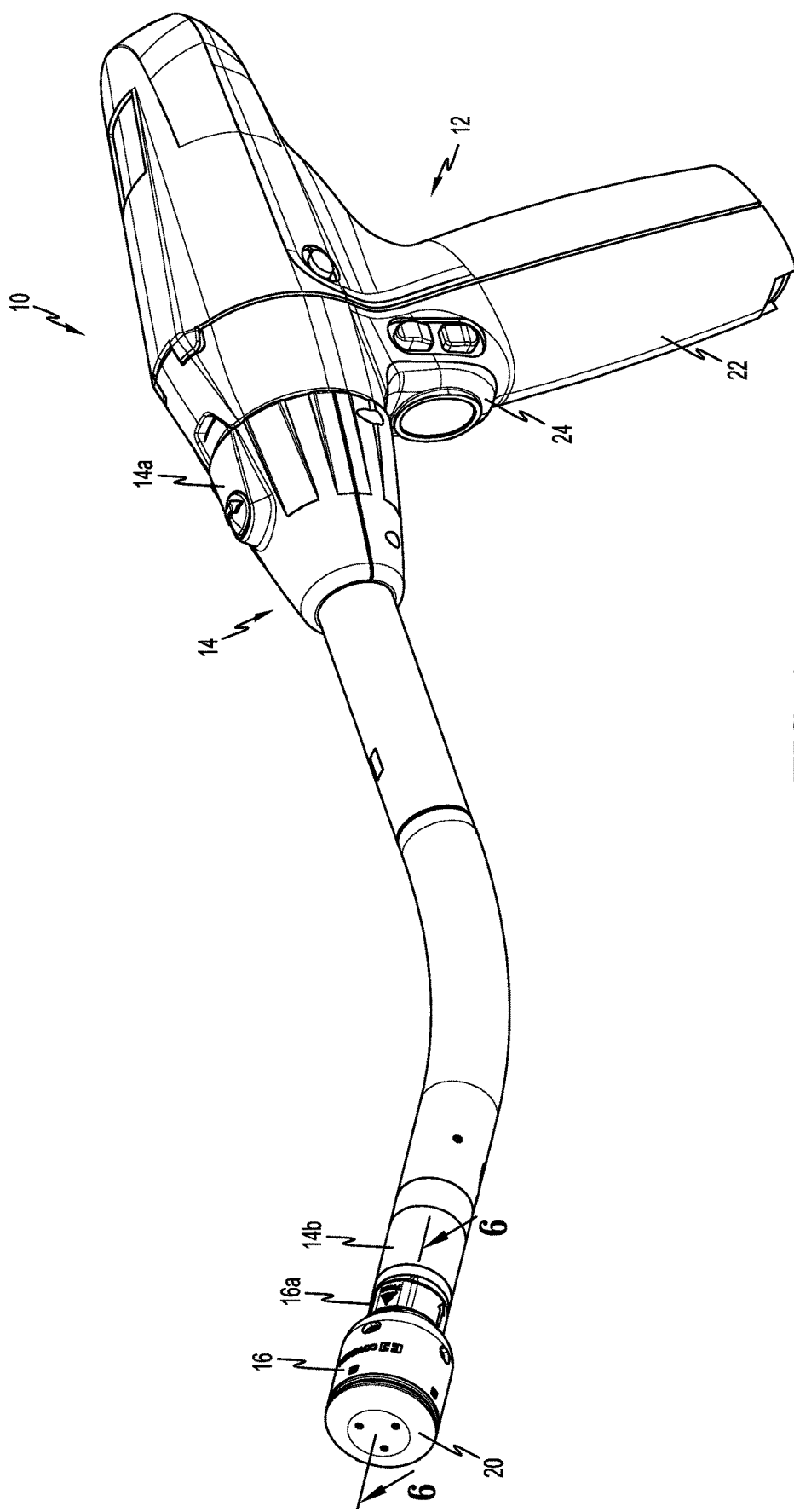
FIG. 1 is a perspective view of a circular stapling device.
Figure 2:
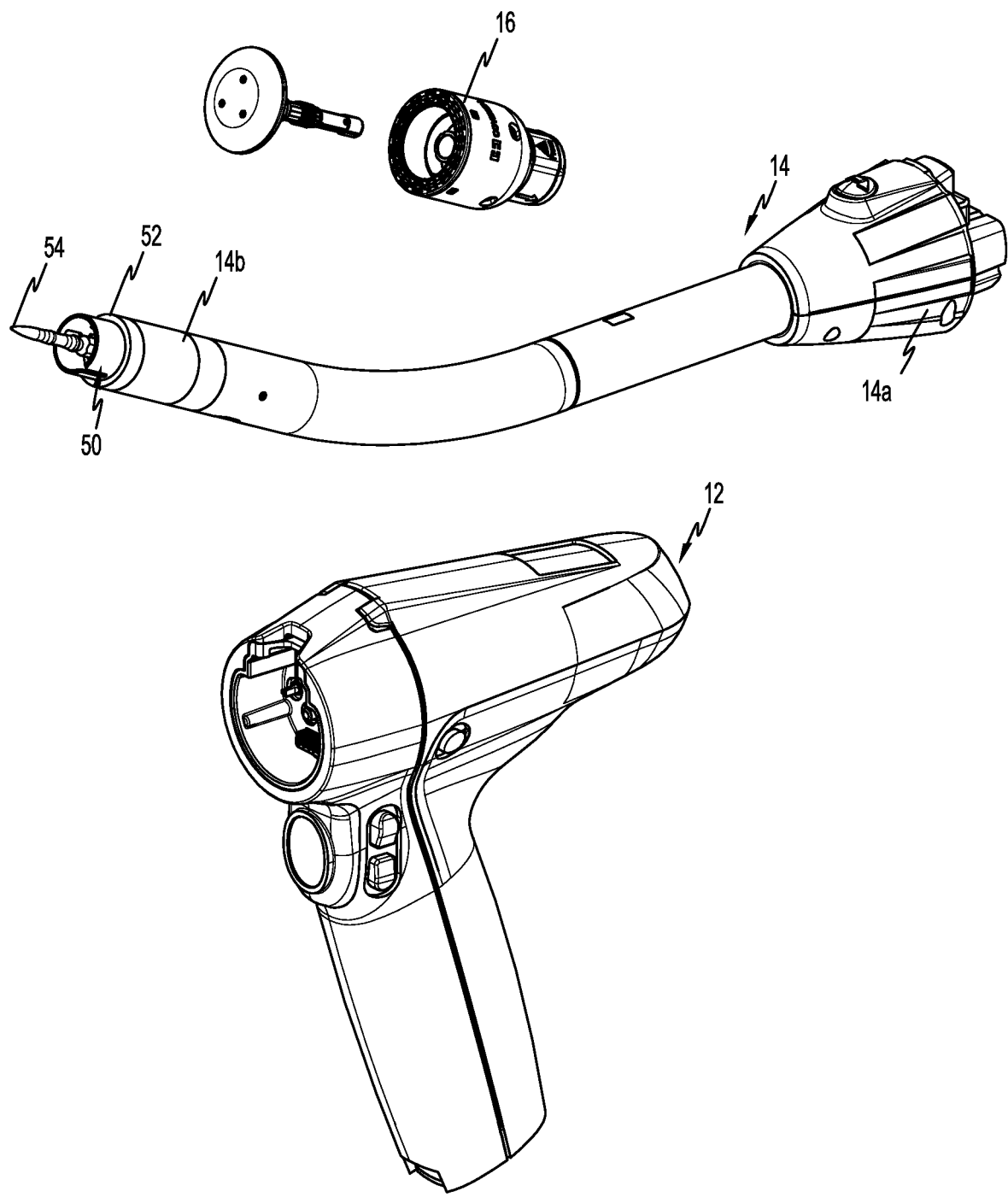
FIG. 2 is a perspective view of a handle assembly, an adaptor assembly, a reload assembly, and an anvil of the circular stapling device of FIG. 1 separated from each other.

FIGS. 1 and 2 illustrate a circular stapling device 10 including a handle assembly 12, an elongate body or adaptor assembly 14, a reload assembly 16 releasably supported on the adaptor assembly 14, and an anvil assembly 20 releasably supported for movement in relation to the reload assembly 16 between an open position (not shown) and a clamped position (FIG. 1).

The reload assembly 16 includes a proximal portion 16a that can be releasably coupled to a distal portion 14b of the adaptor assembly 14 and the adaptor assembly 14 includes a proximal portion 14a that can be releasably coupled to the handle assembly 12. The handle assembly 12 includes a stationary grip 22 that supports actuation buttons 24 for controlling operation of various functions of the circular stapling device 10 including approximation of the reload assembly 16 and anvil assembly 20, firing of staples from the reload assembly 16, and cutting or coring of tissue.

The circular stapling device 10 is illustrated as an electrically powered stapling device including an electrically powered handle assembly 12 that may support one or more batteries (not shown). The adaptor assembly 14 translates power from the handle assembly 12 to the reload and anvil assemblies 16, 20, respectively, to staple and cut tissue. It is envisioned that the disclosed aspects could also be incorporated into a stapling device that is configured for use with a robotic system that does not include a handle assembly, or to a stapling device including a manually actuated handle assembly.

A trocar assembly 50 (FIG. 2) is releasably received within the distal portion 14b of the adaptor assembly 14 and configured to operably engage the anvil assembly 20. The trocar assembly 50 includes and a trocar member 54 slidably disposed relative to the housing 52 of the adaptor assembly 14.

Figure 3A:
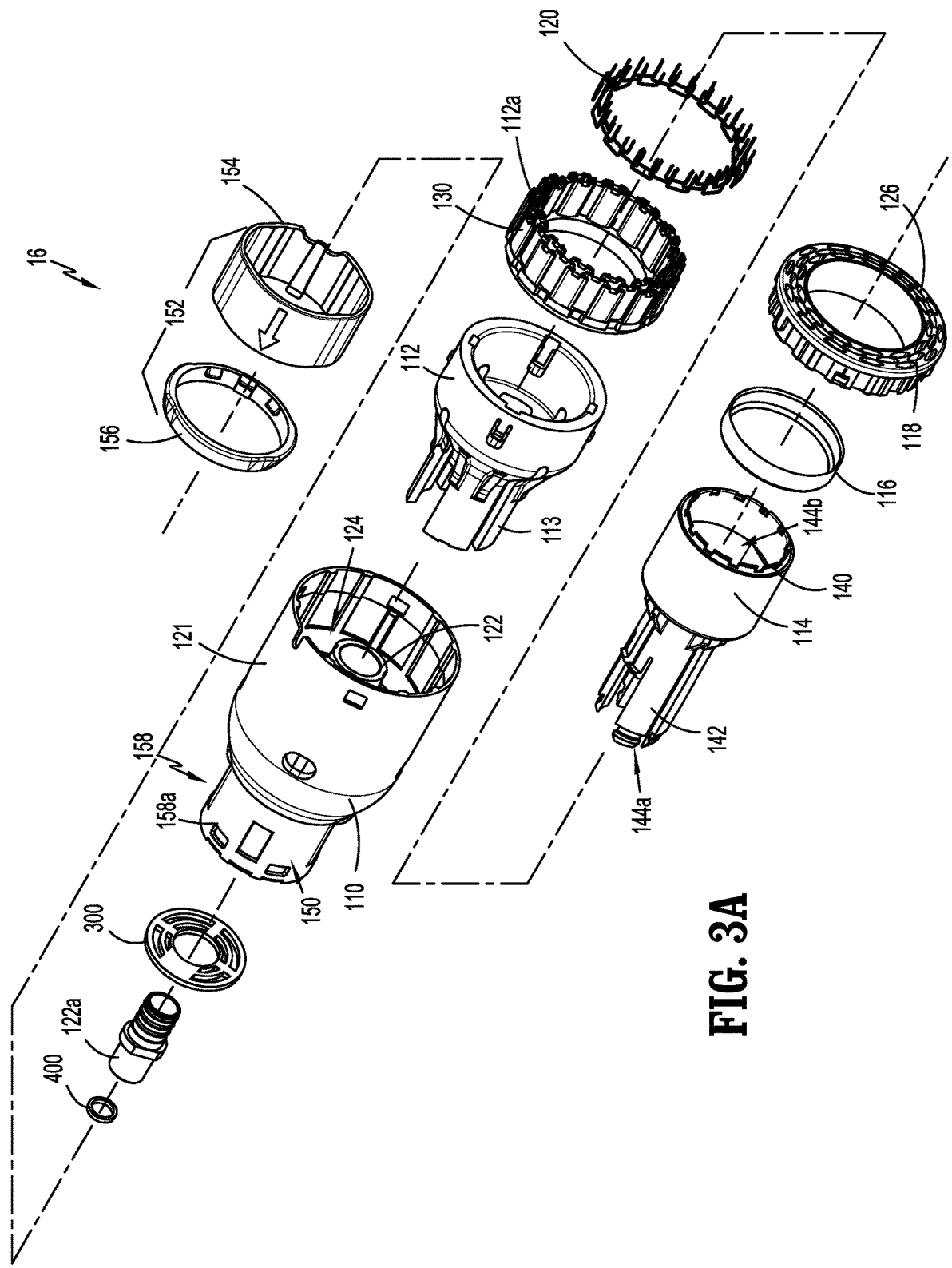
FIG. 3A is a side perspective exploded view of the reload assembly of FIG. 2.

FIG. 3A illustrates an exploded view of the reload assembly 16 which includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The shell housing 110 includes an outer housing portion 121 and an inner housing portion 122 that are spaced from each other to define an annular cavity 124 between the outer and inner housing portions 121 and 122. The inner housing portion 122 supports a bushing 122a that provides stability to the shell housing 110. The staple actuator 112 and the staple pushing member 112a are movable within the annular cavity 124 of the shell housing 110 from a retracted position to an advanced position to eject the staples 120 from the staple cartridge 118 as described in further detail below.

The staple cartridge 118 is annular and defines an annular array of staple pockets 126. Each of the staple pockets 126 supports one of the staples 120. The staple actuator 112 and the staple pushing member 112a together define a longitudinal through bore that receives the knife carrier 114. The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 16 has a plurality of fingers 130. Each of the plurality of fingers 130 is received within a respective one of the staple pockets 126 of the staple cartridge 118 and is movable through the respective staple pocket 126 to eject the staples 120 from the staple pockets 126 when the staple pushing member 112a is moved from a retracted position to an advanced position within the shell housing 110.

The knife carrier 114 is received within the longitudinal through bore of the staple actuator 112 and includes a distal body portion 140 and a plurality of spaced longitudinally extending proximal body portions 142. The distal body portion 140 and the proximal body portions 142 define a stepped central bore having a proximal portion 144a and a distal portion 144b. The proximal portion 144a of the stepped central bore of the knife carrier 114 is received about the inner housing portion 122 of the shell housing 110 such that the knife carrier 114 is movable within the staple actuator 112 about the inner housing portion 122 of the shell housing 110 between a retracted position and an advanced position. The annular knife 116 is coupled to or supported on the distal body portion 140 of the knife carrier 114. The proximal body portions 142 of the knife carrier 114 defines slots 148 that receive guide portions 115 of the shell housing 110 to limit the knife carrier 114 to longitudinal movement within the shell housing 110.

The shell housing 110 includes a proximal portion 150 that supports a coupling mechanism 152. The coupling mechanism 152 is operable to releasably couple the reload assembly 16 to the adaptor assembly 14 of the stapling device 10 (FIG. 1) to facilitate replacement of the reload assembly 16 and reuse of the stapling device 10. The coupling mechanism 152 includes a retaining member 154 and a coupling member 156. The retaining member 154 secures the coupling member 156 to the shell housing 110. The coupling member 156 is received about the proximal portion 150 of the shell housing 110 and is configured to engage the distal portion of the adaptor assembly 14 (FIG. 1) to couple the adaptor assembly 14 to the reload assembly 16. It is envisioned that other types of coupling mechanisms can be used to secure the reload assembly 16 to the distal portion of the adaptor assembly 14.

In certain aspects of the disclosure, the reload assembly 16 of the stapling device 10 is designed to be disposable and the handle assembly 12 and the adaptor assembly 14 are designed to be reprocessed or resterilized and reused. As such, the reload assembly 16 and components that form the reload assembly 16 are formed of materials, e.g., plastics, that are less costly and less durable than materials e.g., stainless steel, used to form the handle assembly 12 and/or the adaptor assembly 14.

The shell housing 110 of the reload assembly 16 is molded of a plastic material (e.g., polycarbonate, polyethylene, nylon, etc.) and includes a proximal portion 158 having a tubular extension 158a that extends proximally from the outer housing portion 121 of the shell housing 110. The tubular extension 158a defines a cylindrical cavity 164 that is dimensioned to receive the distal portion 14b (e.g., housing 52 shown in FIG. 2) of the adaptor assembly 14. The coupling mechanism 152 is supported about the tubular extension 158a of the proximal portion 158 of the shell housing 110 and is operable to secure the reload assembly 16 to the adaptor assembly 14.

Figure 3B:
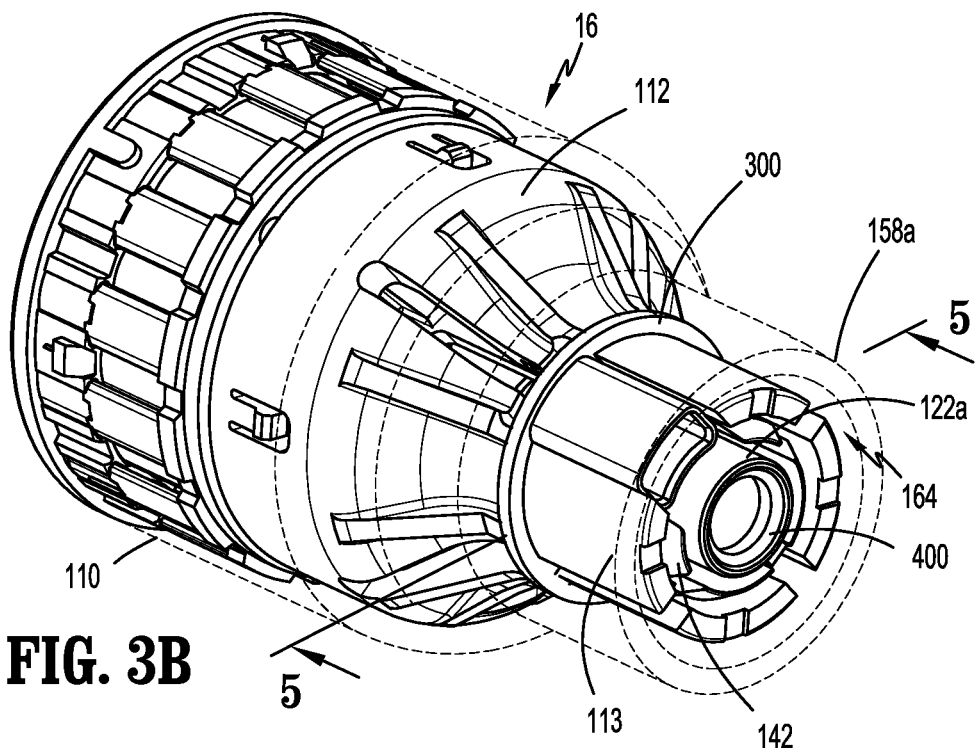
FIG. 3B is a rear perspective view of the reload assembly of FIG. 2 with a shell illustrated in phantom.
Figure 5:
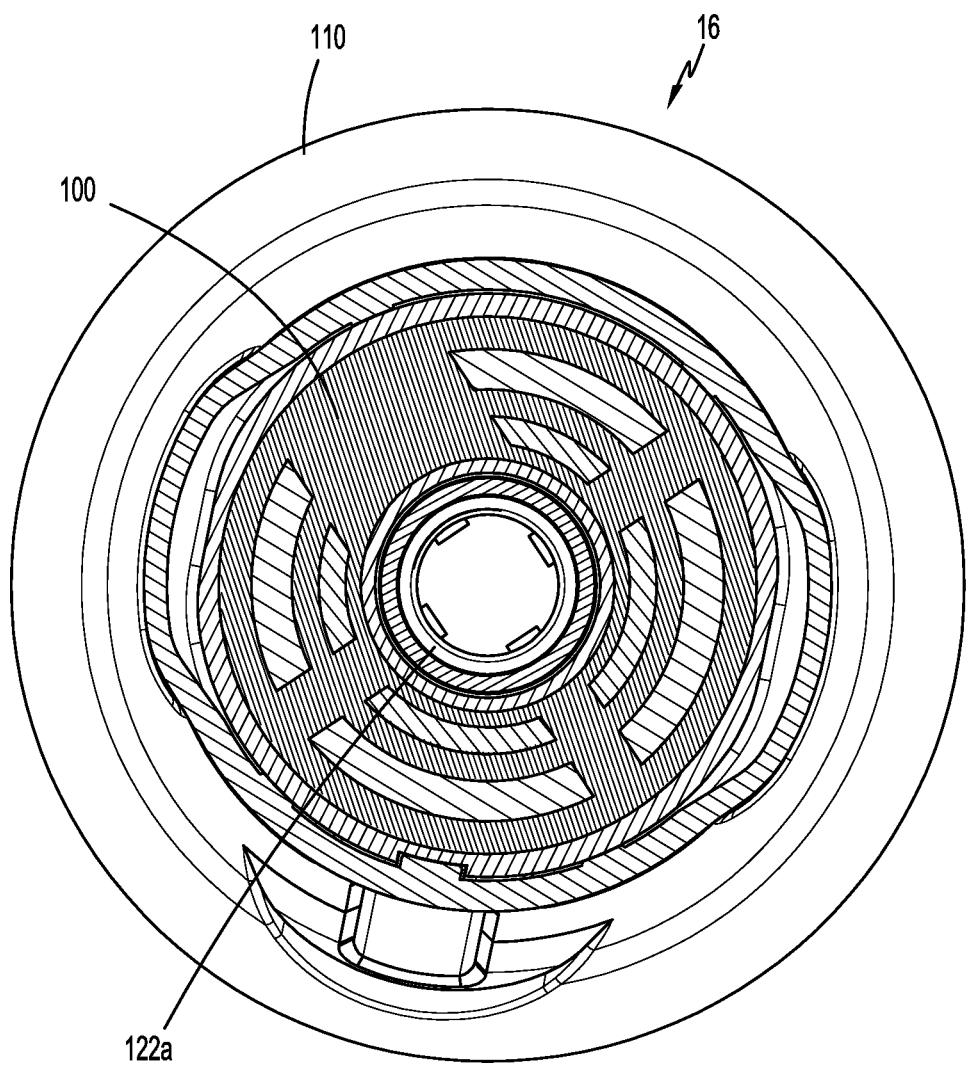
FIG. 5 is a rear cross-sectional view of the reload assembly of FIG. 2 taken along line 5-5 of FIG. 3B.
Figure 6:
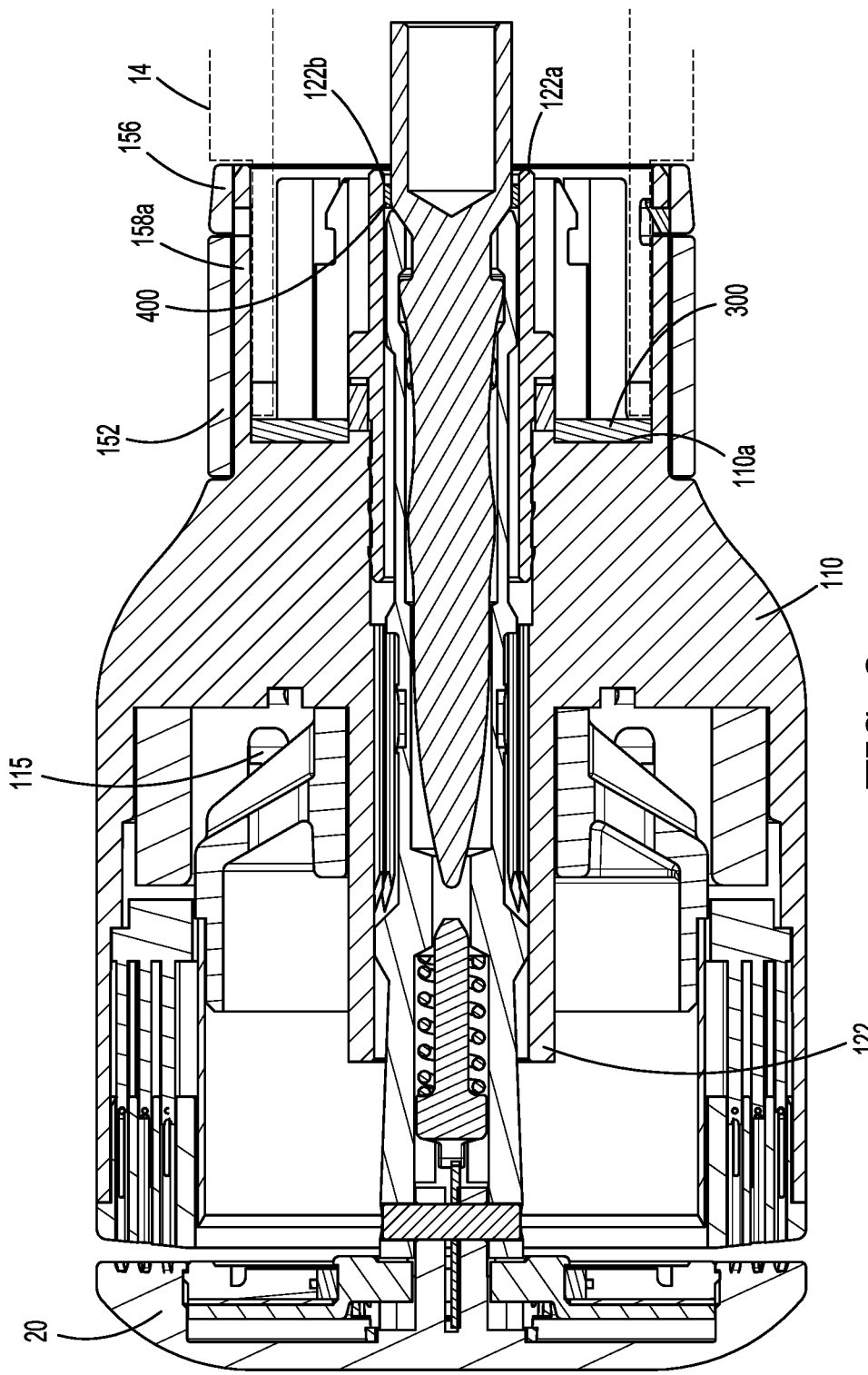
FIG. 6 is a side cross-sectional view of a distal portion of the circular stapling device of FIG. 1 taken along line 6-6.

FIGS. 3B, 5, and 6 illustrate the reload assembly 16 including a first seal 300 and a second seal 400 configured to prevent fluid ingress into components of the reload assembly 16 and components of the stapling device 10 including the adaptor assembly 14 to which the reload assembly 16 is coupled. As described above, the reload assembly 16 includes a shell housing 110 defining a cavity 124. The first seal 300 is disposed within the cavity 124 and defines a staple actuator opening 302, a knife carrier opening 304, and a central opening 306.

The staple actuator 112 is disposed within the cavity 124 of the shell housing 110 and is movable relative to the shell housing 110 to eject the plurality of staples 120 from the staple cartridge 118. The staple actuator 112 includes proximally extending legs 113 that extend through the staple actuator openings 302 of the first seal 300 such that the first seal provides a fluid seal about each the proximally extending legs 113.

The knife carrier 114 is also disposed within the cavity 124 of the shell housing 110 and is movable relative to the shell housing 110. The knife carrier 114 includes a proximally extending body portion 142 that extends proximally through the knife carrier opening 304 of the first seal 300 to provide a fluid seal about the body portion 142.

Figure 4:
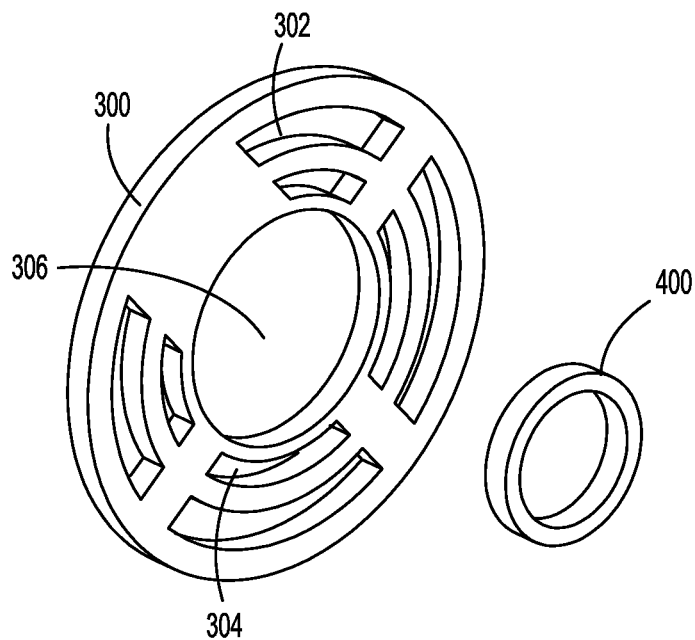
FIG. 4 is a perspective view of a first seal and a second seal of the reload assembly of FIG. 2.

As illustrated in FIG. 4, in aspects, the first seal 300 may include a plurality of staple actuator openings 302 and a plurality of knife carrier openings 304. Additionally, in aspects, the one or more staple actuator openings 302 and knife carrier openings 304 may be curved along a surface of the first seal 300 to match a curved shape of the proximal legs 113 of the staple actuator 112 and the proximal body portions 142 of the knife carrier 114. As the staple actuator 112 is distally advanced to eject the staples 120 from the staple cartridge 118, each proximal leg 113 of the staple actuator 112 slides through a respective staple actuator opening 302 of the first seal 300 while maintaining a fluid seal between each proximal leg 113 and the first seal 300. Similarly, as the knife carrier 114 is distally advanced to cut tissue, each proximal body portion 142 of the knife carrier 114 slides through a respective knife carrier opening 304 of the first seal 300 while maintaining a fluid seal between each proximal body portion 142 and the first seal 300. In this manner, a fluid seal is maintained between the distal portion of the reload assembly 16, where tissue, fluid and other contaminants are present, and a proximal portion of the reload assembly 16, where the reload assembly 16 couples to the other components of the surgical stapler 10 (e.g., adaptor assembly 14).

As described above, the reload assembly 16 includes a bushing 122a disposed within a cylindrical cavity 164 defined by the shell housing 110. The bushing 122a is configured to receive a trocar member 54 (FIG. 2) therethrough. The second seal 400 is operably coupled to an inner annular surface 122b of the bushing 122a such that a fluid seal is formed between the bushing 122a and the trocar member 54 when the trocar member 54 is positioned therethrough. In an aspect, the second seal 400 is coupled to the inner annular surface 122b of the bushing 122a by an adhesive or glue, and/or may be dimensioned to friction-fit therein. Additionally, or alternatively, a recess or protrusion (not shown) may be defined along the inner annular surface 122b of the bushing 122a and the second seal 400 may be positioned within the recess or against the protrusion to present longitudinal movement of the second seal 400 within the bushing 122a. Additionally, a portion of the bushing 122a may be positioned through the central opening 306 of the first seal 300.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A stapling device comprising:
a handle assembly;
an adaptor assembly extending from the handle assembly, the adaptor assembly having a distal end portion; and
a reload assembly supported on the distal end portion of the adaptor assembly, the reload assembly including:

a shell housing defining a cavity and having a proximal portion and a distal portion;

a staple cartridge supported on the distal portion of the shell housing, the staple cartridge supporting a plurality of staples;

a first seal disposed within the cavity and defining a staple actuator opening and a knife carrier opening;

a staple actuator disposed within the cavity of the shell housing and movable relative to the shell housing to eject the plurality of staples from the staple cartridge, the staple actuator including a proximal leg extending through the staple actuator opening of the first seal to provide a fluid seal between the proximal leg and the first seal; and a knife carrier disposed within the cavity of the shell housing and movable relative to the shell housing, the knife carrier including a proximal body portion extending through the knife carrier opening of the first seal to provide a fluid seal between the proximal body portion and the first seal.

2. The stapling device of claim 1, wherein the staple actuator defines a longitudinal bore and the knife carrier is movable through the longitudinal bore.

3. The stapling device of claim 1, wherein the reload assembly further includes a knife secured to the knife carrier, the knife being movable with the knife carrier as the knife carrier is moved.

4. The stapling device of claim 3, wherein the knife includes an annular cutting edge.

5. The stapling device of claim 1, further comprising a coupling mechanism adapted to secure the reload assembly to the distal end portion of the adaptor assembly.

6. The stapling device of claim 1, wherein the shell housing defines a cylindrical cavity, the reload assembly further includes a bushing disposed within the cylindrical cavity, and the adaptor assembly includes a trocar, the bushing configured to receive the trocar of the adaptor assembly therethrough.

7. The stapling device of claim 6, wherein the bushing defines an inner annular surface and the reload assembly further includes a second seal received within the inner annular surface of the bushing such that a fluid seal is formed between the bushing and the trocar when the trocar is positioned therethrough.

8. The stapling device of claim 6, wherein the first seal defines a central opening and the bushing is positioned through the central opening.

9. The stapling device of claim 1, wherein the proximal leg of the staple actuator defines a curved shape and the first seal defines a surface, the staple actuator opening of the first seal being curved along the surface of the first seal to match the curved shape of the proximal leg of the staple actuator.

10. A reload assembly comprising:

a shell housing defining a cavity and having a proximal portion and a distal portion;

a staple cartridge supported on the distal portion of the shell housing, the staple cartridge supporting a plurality of staples;

a first seal disposed within the cavity and defining a staple actuator opening and a knife carrier opening;

a staple actuator disposed within the cavity of the shell housing and movable relative to the shell housing to eject the plurality of staples from the staple cartridge, the staple actuator including a proximal leg extending proximally therefrom and through the staple actuator opening of the first seal to provide a fluid seal between the proximal leg and the first seal; and a knife carrier disposed within the cavity of the shell housing and movable relative to the shell housing, the knife carrier including a proximal body portion extending proximally therefrom and through the knife carrier opening of the first seal to provide a fluid seal between the proximal body portion and the first seal.

11. The reload assembly of claim 10, wherein the staple actuator defines a longitudinal bore and the knife carrier is movable through the longitudinal bore.

12. The reload assembly of claim 10, further comprising a knife secured to the knife carrier, the knife movable with the knife carrier as the knife carrier is moved.

13. The reload assembly of claim 12, wherein the knife includes an annular cutting edge.

14. The reload assembly of claim 10, wherein the shell housing defines a cylindrical cavity, the reload assembly further includes a bushing disposed within the cylindrical cavity, the bushing configured to receive a trocar of an adaptor assembly therethrough.

15. The reload assembly of claim 14, wherein the bushing defines an inner annular surface and the reload assembly further includes a second seal received within the inner annular surface of the bushing such that a fluid seal is formed between the bushing and the trocar when the trocar is positioned therethrough.

16. The reload assembly of claim 14, wherein the first seal defines a central opening and the bushing is positioned through the central opening.

17. The reload assembly of claim 10, wherein the proximal leg of the staple actuator defines a curved shape and the first seal defines a surface, the staple actuator opening of the first seal being curved along the surface of the first seal to match the curved shape of the proximal leg of the staple actuator.

* * * * *